United States Patent [19]

Itoh et al.

[11] Patent Number: 4,636,465

[45] Date of Patent: Jan. 13, 1987

[54] METHOD AND COMPOSITION FOR DETERMINATION OF GLYCEROL

[75] Inventors: Nobuya Itoh, Suzuka; Kuniyoshi Matsunaga, Ichinomiya, both of Japan

[73] Assignee: Amano Pharmaceutical Co., Ltd., Nagoya, Japan

[21] Appl. No.: 601,252

[22] Filed: Apr. 17, 1984

[30] Foreign Application Priority Data

Apr. 21, 1983 [JP] Japan ................................ 58-70730

[51] Int. Cl.$^4$ ........................ C12Q 1/48; C12Q 1/44; C12Q 1/32
[52] U.S. Cl. ...................................... 435/15; 435/19; 435/26; 435/810
[58] Field of Search ....................... 435/4, 15, 26, 810, 435/194, 19

[56] References Cited

U.S. PATENT DOCUMENTS 3,703,591 11/1972 Bucolo et al. ......................... 435/15
4,273,870 6/1981 Möllering et al. ..................... 435/26

OTHER PUBLICATIONS

Lerner et al, Biochim. Biophys. Acta, 615: 1–9 (1980).
Boobis et al, Chemical Abstracts, 99:118623c, 322 (1983).
Hers, Methods in Enzymology, vol. V, Colowick et al (ed)., Academic Press, New York, 362–364 (1962).
Weinhouse et al, J. Bact., 127(2): 747–754 (1976).

*Primary Examiner*—Esther M. Kepplinger

[57] ABSTRACT

A method for determination of glycerol by using a reagent system comprising glycerol dehydrogenase and a pyridine nucleotide coenzyme, characterized in that an enzyme selected from the group consisting of triokinase and dihydroxyacetone kinase is incorporated into the reagent system to eliminate the formed dihydroxyacetone or D-glyceraldehyde in the assay system.

12 Claims, 6 Drawing Figures

METHOD AND COMPOSITION FOR DETERMINATION OF GLYCEROL

BACKGROUND OF THE INVENTION

1. Field of the Invention

The present invention relates to a method and composition for determination of glycerol, and particularly to a method and composition for determination of glycerol by using glycerol dehydrogenase, characterized in that the glycerol dehydrogenase-catalyzed reaction for the determination is promoted by dihydroxyacetone kinase or triokinase. The invention is specially useful for the determination of glycerol and triglyceride be contained within biological fluids.

2. Description of the Prior Art

The determination of glycerol and triglyceride contained within blood is very important for diagnosis of hyperlipemia. In particular, hypercontent of triglyceride in blood is characteristic of arteriosclerosis, coronary insufficiency, myocardial infarction, etc. For early diagnoses or treatments of these diseases, a rapid and accurate method is desired for determination of triglyceride content in blood.

A method for determination of triglyceride using lipase and glycerol dehydrogenase is characterized by the following reaction sequence.

Glycerol +

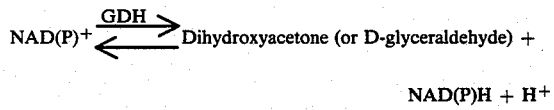

NAD(P)H + H+

NAD(P)+ represents nicotinamide adenine dinucleotide (phosphate), NAD(P)H represents reduced NAD(P)+, and GDH represents glycerol dehydrogenase.

First, triglyceride is hydrolyzed into glycerol and fatty acids by the action of lipase, then the glycerol is oxidized into dihydroxyacetone (or D-glyceraldehyde) in the presence of NAD(P)+ by the action of glycerol dehydrogenase. The formed NAD(P)H is measured by spectrophotometrical or fluorometrical assay, thereby determining glycerol and consequently triglyceride.

The equilibrium of the above GDH-catalyzed reaction is shifted in the reverse direction. Thus, the reaction does not sufficiently proceed in the forward direction. In addition, it takes a long time to attain equilibrium. Consequently, the measurement is unsatisfactory in precision or sensitivity, and the range of measurable glycerol or triglyceride concen- trations.

In order to overcome the above difficulty, it was necessary to carry out the reaction in as high pH as from 10 to 11, or to add excess NAD(P)+ to the reaction mixture.

A possible preferable approach to the promotion of the above GDH-catalyzed reaction is to eliminate the product dihydroxyacetone or D-glyceraldehyde from the assay system. For example, the method of converting the dihydroxyacetone into the corresponding hydrazone by adding hydrazine was attempted to promote the GDH-catalyzed reaction [Rinshobyori (Clinical Pathology), 24, 855 (1976)]. However, this method is unsatisfactory, since the enzyme is inactivated by hydrazine during the reaction.

SUMMARY OF THE INVENTION

An object of the invention is to provide a method for determination of glycerol which can overcome the above-mentioned problems.

Thus, an object of the invention is to provide a method for determination of glycerol by using GDH, wherein the reaction can be effectively promoted under the conditions favorable for enzymes.

Another object of the invention is to provide such a reagent composition for determination of glycerol by using GDH that is effective for promoting the GDH-catalyzed reaction under favorable conditions for enzymes.

According to the present invention, there is provided a method for determination of glycerol by using a reagent system comprising GDH and a pyridine nucleotide coenzyme, characterized in that an enzyme selected from the group of consisting of triokinase and dihydroxyacetone kinase is incorporated into the reagent system to eliminate the formed dihydroxyacetone or D-glyceraldehyde in the assay system.

According to the present invention, there is provided a composition for determination of glycerol which comprises (1) an enzyme selected from triokinase and dihydroxyacetone kinase, (2) glycerol dehydrogenase, (3) a pyridine nucleotide coenzyme, (4) a phosphate donor, and (5) a divalent metal cation.

DETAILED DESCRIPTION OF THE PREFERRED EMBODIMENTS

Figure 1:
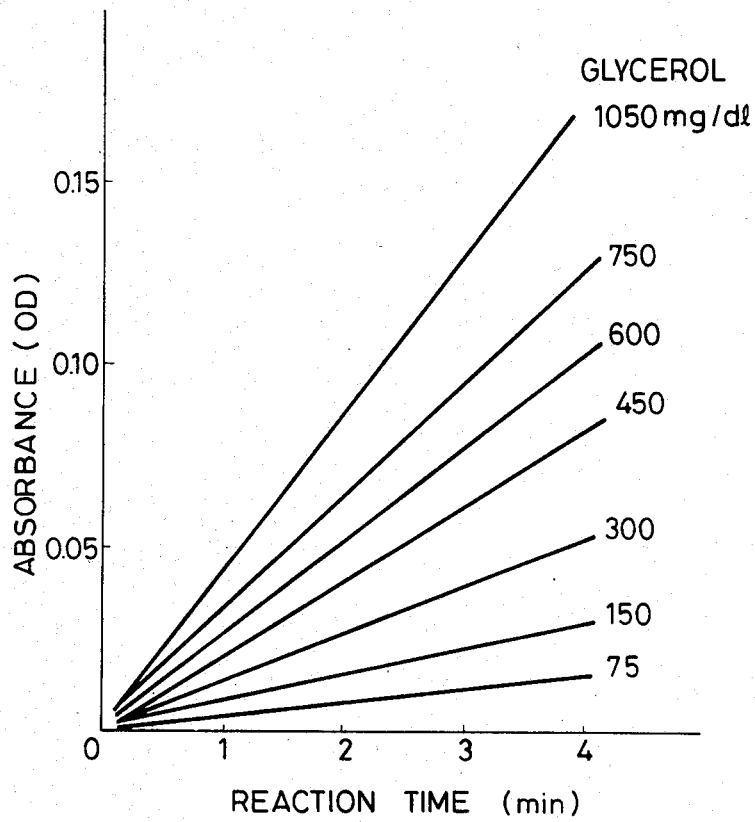
FIG. 1 shows the relation between the reaction time and the change in the absorbance of the reaction mixture, in the determination of glycerol according to the invention.
Figure 2:
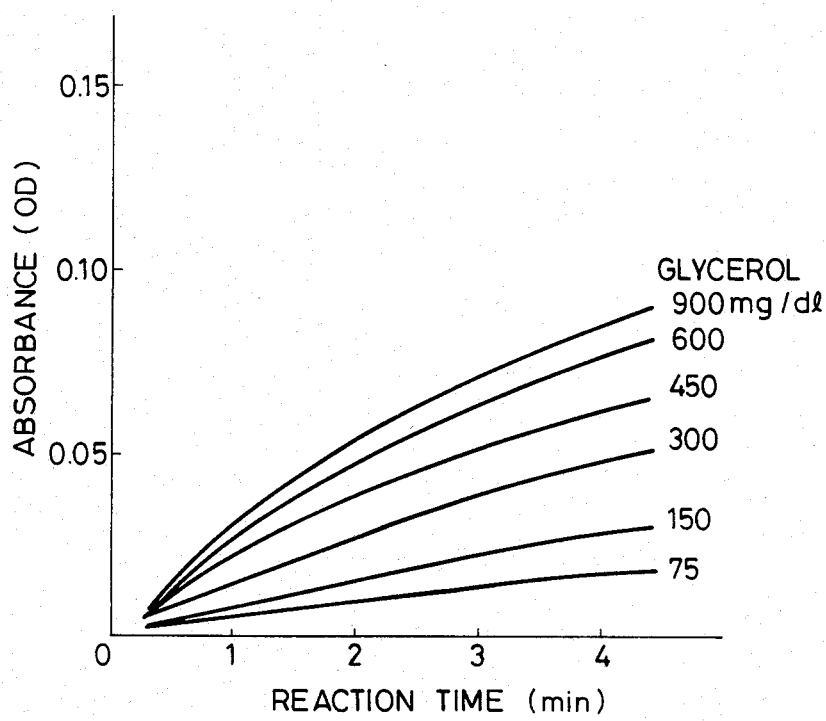
FIG. 2 shows the same relation in a comparative example.

Triokinase (ATP: D-glyceraldehyde-3-phosphotransferase EC 2.7.1.28) is an enzyme which catalyzes the reaction of transferring the phosphate group of a phosphate donor such as adenosine-5'-triphosphate (referred to as ATP) to D-glyceraldehyde as shown by the following equation:

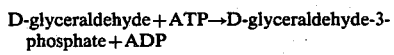

Triokinase is known to catalyze the phospholylation of dihydroxyacetone (referred to as DHA) and D-glyceraldehyde at nearly the same rate.

Dihydroxyacetone kinase (referred to as DHAK) is an enzyme which catalyzes the reaction of transferring the phosphate group of phosphate donor such as ATP to dihydroxyactone but acts only slightly on D- glyceraldehyde and therefore is regarded to be different from triokinase. The reaction of dihydroxyacetone kinase is represented by the following equation:

Dihydroxyacetone+ATP→Dihydroxyacetone phosphate+ADP

Triokinase is known to exist in guinea pig liver, rat liver, and *Bacillus subtilis* [Meth. Enzymol. 5, 362 (1962); Eur. J. Biochem., 31, 59 (1972), and The Enzyme, 2nd ed., 6, 75 (1962)]. Dihydroxyacetone kinase has been found in *Candida methylica* [Z. Allg. Mikrobial., 389 (1980) and ibid., 21, 219 (1981)], *Gluconobacter suboxydans* (Joint Technical Meeting held by the Chubu Blanch and the Kansai Blanch of the Agricultural Chemical Society of Japan, Oct. 9, 1981, Abstract of the lectures, page 3), *Acetobacter xylinum* (J. Bacteriol., 127, 747 (1976)], *Dunaliella*, a green alga, [Plant Physiol., 59, 15 (1977), and Biochim. Biophys. Acta, 615, 1 (1980)]. The present inventors newly found that dihydroxyacetone kinase is abundantly produced by the strains of genus *Schizosaccharomyces*.

All the above cited triokinases and dihydroxyacetone kinases can be used for the invention, the dihydroxyacetone kinase produced by genus *Schizosaccharomyces* is particularly preferable for its productivity and properties.

Available dihydroxyacetone kinase-producing strains of genus *Schizosaccharomyces*, include, for example, *S. pombe* IFO 0340 and IFO 0354, *S. malidevorans* IFO 1608, *S. japonicus* IFO 1609, and *S. octosporus* IAM 12257. Among these, *S. pombe* IFO 0354 is preferred for its high productivity. All the strains above-mentioned have been deposited in recognized depositories respectively, abbreviated mark of "IFO" therein representing Institute for Fermentation, Osaka, Japan, and "IAM" representing Institute of Applied Microbiology, University of Tokyo, Japan.

Dihydroxyacetone kinase produced by *S. pombe* IFO 0354 comprises two isoenzymes (referred to as DHAK(I) and DHAK(II), properties of them are as follows:

(1) Reaction: The enzymes catalyze the reaction of transferring the phosphate group of a phosphate donor such as ATP to DHA to form dihydroxyacetone phosphate.

(2) Substrate specificity: The enzymes act on dihydroxyacetone, but slightly on DL-glyceraldehyde, and not on glycerol, 1,2-propanediol, 1,3-propanediol, acetol, acetoin, glycerol-3- phosphate, or DL-glyceric acid.

(3) Specificity of the enzymes for phosphate donor :ATP is best phosphate donor and uridine-5'-triphosphate slightly acts as a phosphate donor for both DHAK(I) and DHAK(II). Inosine-5'-triphosphate, cytidine-5'-triphosphate, and guanosine-5'-triphosphate are inert.

(4) Specificity for divalent metal cation: The enzymes exhibit no activity in the absence of divalent metal cation such as $Mg^{2+}$, $Ca^{2+}$, $Co^{2+}$, or $Mn^{2+}$. DHAK(I) exhibits the maximum activity in the presence of $Ca^{2+}$ and DHAK(II) in the presence of $Mg^{2+}$.

(5) Optimum pH: Approximately 7.3 for both DHAK(I) and DHAK (II).

(6) pH Stability: DHAK(I) is stable in a pH range of from 5 to 11, and DHAK(II) from 6 to 11.

(7) Optimum temperature:

The optimum temperature is about 60° C. for DHAK(I) and about 55° C. for DHAK(II).

(8) Thermal stability: DHAK(I) is stable below 50° C. and DHAK(II) below 40° C.

(9) Km values: Michaelis constants (Km values) for dihydroxyacetone, DL-glyceraldehyde, and ATP under the reaction conditions of at pH 7.5 and at 25° C. are as follows:

DHAK(I): $8.4 \times 10^{-6}M$, $2.1 \times 10^{-5}M$, $2.2 \times 10^{-4}M$
DHAK(II): $2.0 \times 10^{-5}M$, $3.2 \times 10^{-5}M$, $9.1 \times 10^{-4}M$ DHAK(I) and DHAK(II) exhibit the sufficient activities at 4 mM or above concentration of $Mg^{2+}$.

(10) Molecular weight: Molecular weights of DHAK(I) and DHAK(II), as measured by gel filtration method with Sephadex G-200 (Pharmacia Fine Chemicals Co.), were both calculated to be about 145,000.

Preferred embodiments are described below of the method for determination of glycerol according to the invention. First, glycerol is dehydrogenated into dihydroxyacetone or D-glyceraldehyde by the action of GDH in the presence of $NAD(P)^+$. The formed dihydroxyacetone or D-glyceraldehyde is converted into dihydroxyacetone phosphate or D-glyceraldehyde-3phosphate by the action of triokinase or dihydroxyacetone kinase to eliminate dihydroxyacetone or di-glyceraldehyde from the assay system. Thus. the GDH-catalyzed reaction proceeds rapidly to the end point.

GDH requires a pyridine nucleotide coenzyme such as $NAD^+$ or $NADP^+$. For example; $NAD^+$-dependent GDH (EC 1.1.1.6) from *Escherichia coli*, *Klebsiella pneumoniae*, *Acetobacter suboxydans*, or *Geotrichum candidum* [J. Biol, Chem., 203, 153 (1953), ibid., 235, 1820 (1960), and Agric. Biol, Chem., 46, 3029 (1982)] forms dihydroxyacetone from glycerol; $NADP^+$-dependent GDH (EC 1.1.1.72) from rabbit skeletal muscle [Biochim. Biophys. Acta, 258, 40 (1972)] forms D-glyceraldehyde; and $NADP^+$-dependent glycerol-2-dehydrogenase (EC 1.1.1. 156) from a green alga *Dunaliella parva* [FEBS Letter, 29, 153 (1973)] forms dihydroxyacetone. While any of the above cited GDHs can be used in the invention. GDH from *Geotrichum candidum* is preferred, due to a small Michaelis constant (Km value) for glycerol.

Suitable phosphate donors for use in the invention include, ATP, uridine-5'-triphosphate (UTP), inosine-5'-triphosphate (ITP), cytidine-5'-triphosphate (CTP), and guanosine-5'-triphosphate (GTP). ATP is best phosphate donor for dihydroxyacetone kinase from *Schizosaccharomyces pombe* IFO 0354.

For determining glycerol concentration by the above reaction, it is most convenient to measure the change in the absorbance at 340 nm due to the NAD(P)H formation. Other methods are also applicable such as fluorometry, colorimetry by use of phenazine methosulfate and a tetrazolium salt [Clinica Chimica Acta, 81, 125 (1977)], and colorimetry by use of diaphorase and a tetrazolium salt.

The composition of the invention for determining glycerol contains an enzyme selected from triokinase and dihydroxyacetone kinase, GDH, a pyridine nucleotide coenzyme, a phosphate donor, and a divalent metal cation, as essential components examples of which are as mentioned above. The concentration of each component can be varied over a wide range. For instance, suitable concentrations of GDH are 0.01 to 0.5 u/ml when glycerol is determined by the rate assay system, and is 0.5 u/ml or more when glycerol is determined by the end point assay system. Suitable concentrations of triokinase or dihydroxyacetone kinase are 0.1 u/ml and more.

The reaction is carried out at a pH of 7-9 and at a temperature of 25°-40° C. For the purpose of keeping the pH constant, the reaction mixture is desired to contain a buffer. Any buffer may be employed for this purpose provided that the pH thereof lies in the above-mentioned range, but Tris-HCl buffer (pH 8.0-8.5) is preferable.

The invention is illustrated in more detail with reference to the following examples. Enzymes used in the examples and enzyme assays are described below.

(1) Preparation of dihydroxyacetone kinase

*Schizosaccharomvces pombe* IFO 0354 was inoculated to a medium (pH 6.2) containing 1% malt extract, 0.3% peptone, 0.1% yeast extract, 0.2% $K_2HPO_4$, 0.05% $MgSO_4.7H_2O$, 0.05% KCl, and 0.001% $FeSO_4.7H_2O$. The cultivation was carried out at 30° C. for 48 hours.

The cells were collected by centrifugation from 10 l of the culture broth, suspended in a 20 mM Tris-HCl buffer (pH 7.0), and disrupted with a Dyno Mill KDL. The extract was centrifuged to remove the cell debris, then a polyethyleneimine solution was added to the supernatant up to a concentration of 0.02%, and the resulting precipitate was removed by centrifugation. Then ammonium sulfate was added to the supernatant for the salting-out of the enzyme, and the enzyme precipitate in the fractions of 40-70% saturation was harvested. This precipitate was dissolved in the same buffer, subjected to a Sephadex G-25 gel filtration for desalting, and applied to a DEAE-Sepharose (Pharmacia Fine Chemicals Co.), column equilibrated with the same buffer. After washing the column, the enzyme was eluted with a linear gradient of KCl from 0 to 0.3 M. Two peaks of enzyme activity were observed with DEAET-Sepharose column chromatography. The fractions eluted with 0.12 M KCl (referred to as DHAK(I)) and those eluted with the 0.16 M KCl (referred to as DHAK (II)) were independently collected.

DHAK(I) and DHAK(II) were precipitated by adding ammonium sulfate to combined fractions up to 80% saturation, respectively. Each enzyme precipitates was collected by centrifugation, dissolved in the same buffer, and desalted with Sephadex G-25 column chromatography. Then each resulting enzyme solution was passed through a Blue-Sepharose (Pharmacia Fine Chemical Co.) column previously equilibrated with a 40 mM Tris-HCl buffer (pH 7.0), and active fractions were concentrated by ultrafiltration. Thus, 120 units of DHAK(I) and 360 units of DHAK(II) were obtained. DHAK(I) and DHAK(II) are effective in the mixed state as well. In the following examples, the mixture of DHAK(I) and DHAK(II) thereof was used.

Enzyme assay: The standard assay mixture for measuring the activity of DHAK consists of 1.0 ml of 0.1 M triethanolamine-HCl buffer (pH 7.5), 2.5 mM ATP, 4 mM $MgSO_4$, 0.2 mM NADH, 1.0 mM DHA, 2.5 units of glycerol-3-phosphate dehydrogenase (Boehringer Mannheim GmbH), and 0.01 ml of enzyme solution. The reaction is started by adding enzyme solution, and the decrease in the absorbance at 340 nm is measured spectrophotometrically at 25° C. In the blank assay, DHA is excluded from the reaction mixture. One unit of the enzyme activity is defined as the amount of enzyme which catalyzes the formation of 1 μmol $NAD^+$ in one minute under the above conditions. The above reaction is represented by the following equations:

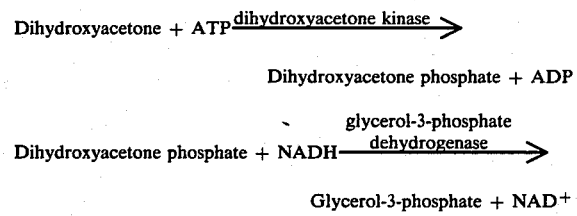

(2) Preparation of triokinase

Triokinase was prepared from swine liver in accordance with the process described in Meth. Enzymol., 5. 362 (1962). The enzyme activity was determined in the same manner of dihydroxyacetone kinase except that D-glyceraldehyde was used in the place of dihydroxyacetone as a substrate.

(3) Preparation of glycerol dehydrogenase (GDH)

GDH from *Geotrichum candidum* and GDH from rabbit skeletal muscle were prepared in accordance with the process described in Agric. Biol. Chem., 46, 3029 (1982) and the process described in Biochim. Biophys. Acta, 258, 48 (1972), respectively. One unit of GDH activity is defined as the amount of enzyme which catalyzes the formation of 1 μmole of NAD(P)H in one minute at 25° C. and pH 8.0 in the reaction of glycerol and $NAD(P)^+$ (4) Expression of lipase activity One unit of lipase activity is defined as the amount of enzyme catalyzing the liberation of 1 μmole of the corresponding fatty acid in one minute at 37° C. and pH 7.0 when the mixture of olive oil emulsion and bovine serum albumin is used as a substrate.

EXAMPLE 1

0.02 ml each of glycerol standard solutions in the range from 75 to 1050 mg/dl as triolein was mixed with 0.96 ml of 0.15 M Tris-HCl buffer (pH 8.5) containing 1.04 mg/ml $MgSO_4.7H_2O$, 2.0 mg/ml NAD and 1.5 mg/ml ATP, in a 1-ml cuvette. The mixture was kept at 37° C. for 3 minutes, then 0.02 ml of 0.02 M Tris-HCl buffer (pH 7.5) containing 8.75 u/ml GDH of *Geotricum candidum* and 25 u /ml dihydroxyacetone kinase was added to the reaction mixture, and the increase in the absorbance at 340 nm was measured. For comparison, the above procedure was repeated on the same reaction system without dihydroxyacetone kinase.

Figure 3:
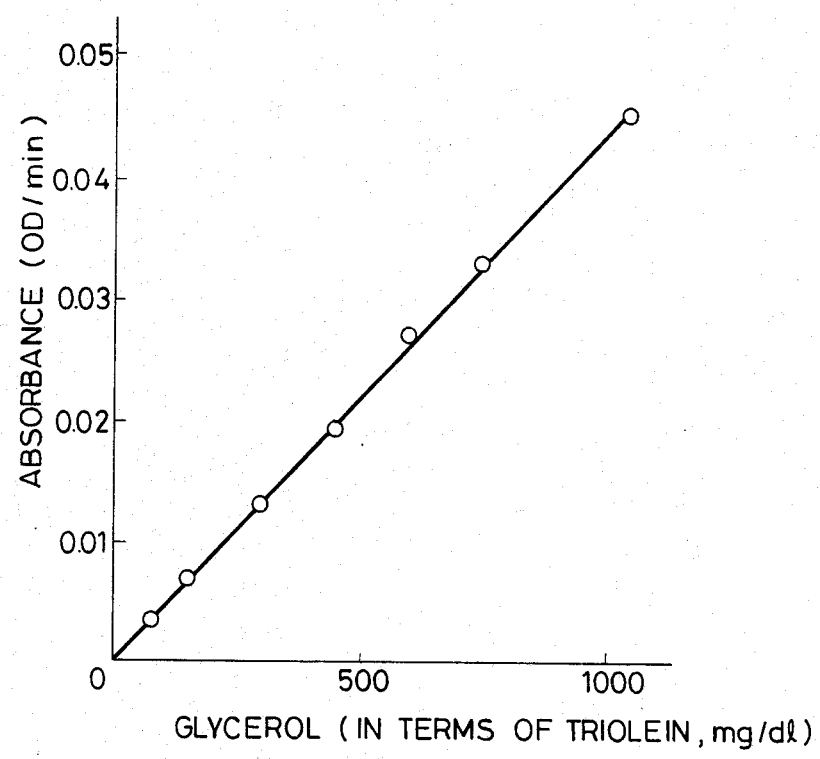
FIGS. 3 and 4 show the calibration curves for the determination of glycerol according to the method of the invention.

Relations between the reaction time and the absorbance are shown in FIGS. 1 (example of the invention) and 2 (comparative example)respectively, and the calibration curve according to the method of the invention is shown in FIG. 3.

It shows that, according to the method of the invention, the reaction rate is constant with respect to the reaction time even at a glycerol concentration as triolein) of higher than 1000 mg/dl and glycerol can be quantitatively determined with a high sensitivity; while according to the method of the comparative example, the reaction rate is low and decreases with time.

EXAMPLE 2

Glycerol was determined in the same manner as in Example 1 using triokinase, GDH of rabbit skeletal muscle, and $NADP^+$ in the place of dihydroxyacetone kinase, GDH of *Geotrichum candidum*, and NAD, respectively. The results were similar to those of Example 1.

EXAMPLE 3

Glycerol was determined in the same manner as in Example 1 using $CaCl_2$, $CoCl_2$, and $MnCl_2$ separately in the place of $MgSO_4$. In all the cases, the results were similar to those of Example 1.

EXAMPLE 4

In test tubes, 1.96 ml portions of a 0.15 M Tris-HCl buffer (pH 8.5) containing 1.04 mg/ml $MgSO_4 \cdot 7H_2O$, 2.0 mg/ml NAD, and 1.5 mg/ml ATP were mixed with 0.02 ml portions of 0.02 M Tris-HCl buffer (pH 7.5) containing 75 u/ml GDH of *Geotrichum candidum* and 25 u/ml dihydroxyacetone kinase. Each mixture was maintained at 37° C. for 3 minutes, then 0.02 ml each of standard glycerol solutions in the range from 75 to 900 mg/dl (as triolein) was added, the reaction was allowed to proceed for 20 minutes at 37° C. and the increase in the absorbance at 340 nm after 20 minutes was measured. For comparison, the above procedure was repeated on the same reaction system without dihydroxyacetone kinase.

Figure 4:
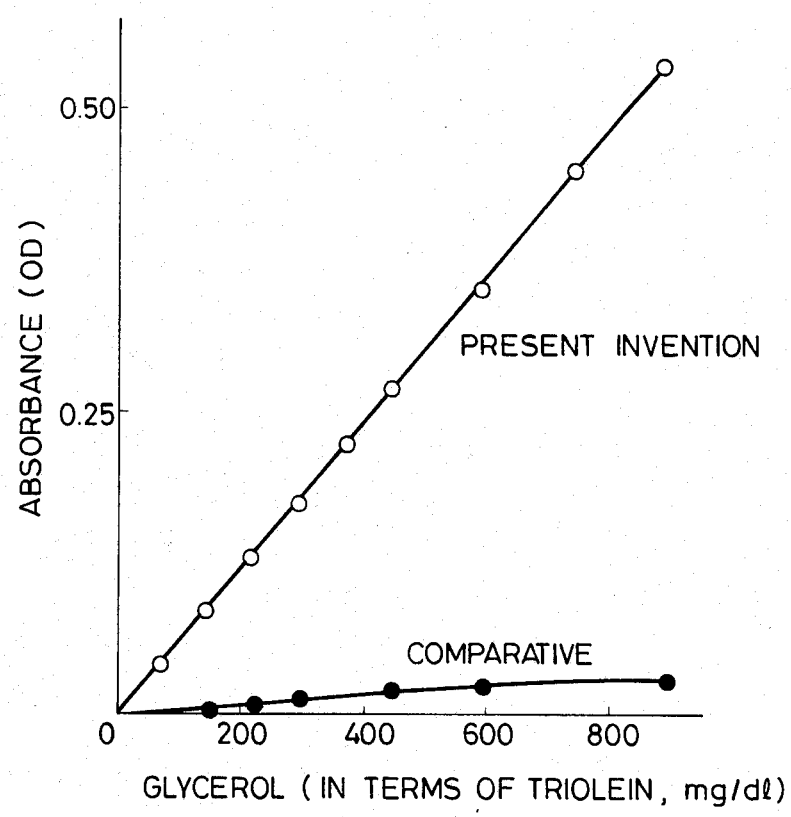

As shown in FIG. 4, the results shows that; according to the method of the invention, the GDH-catalyzed reaction proceeds to the end point, the calibration curve is hence linear up to a glycerol concentration of at least 900 mg/dl (as triolein), and a high sensitive determination of glycerol is possible; while the method of the comparative example results in low reactivity, poor sensitivity, and a non-linear calibration curve.

EXAMPLE 5

Determination of triglyceride

Figure 5:
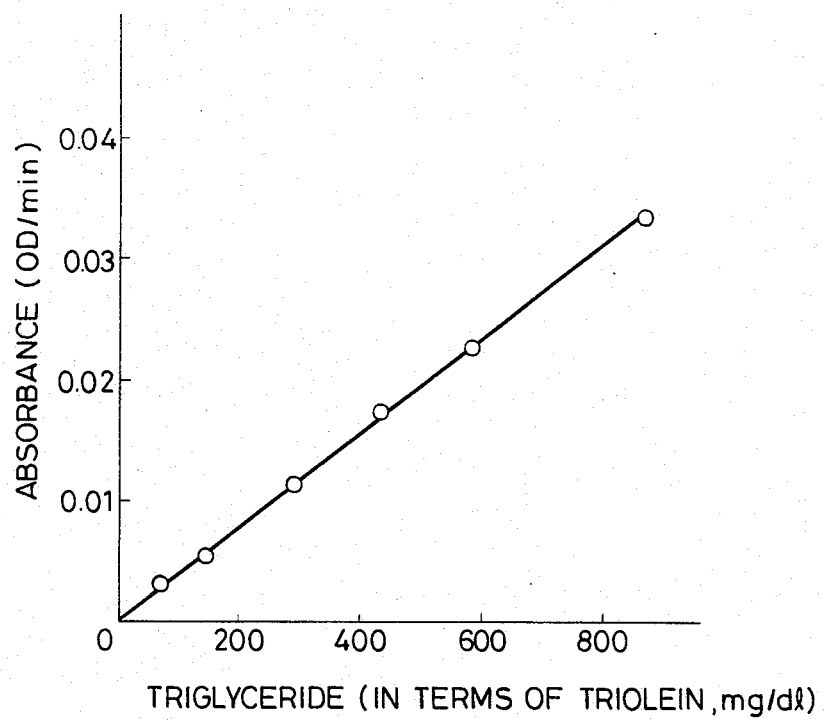
FIG. 5 shows the calibration curve for the determination of triglyceride according to the method of the invention.

Triglyceride concentration was determined by adding lipase (lipoprotein lipase) to samples to hydrolyze the triglyceride, and measuring the quantities of formed glycerol, as follows:

0.02 ml each of serum samples was mixed with 0.96 ml of 0.15 M Tris-HCl buffer (pH 8.5) containing 500 u/ml lipoprotein lipase (Amano Pharmaceutical Co., Ltd.), 1.04 mg/ml $MgSO_4 \cdot 7H_2O$, 2.0 mg/ml NAD, 1.5 mg/ml ATP, and 0.1% Triton X-100, and the mixture was incubated at 37° C. for 5 minutes. Then, 0.02 ml of 0.02 M Tris-HCl buffer (pH 7.5) containing 8.75 u/ml GDH of *Geotrichum candidum* and 25 u/ml dihydroxyacetone kinase was added to the mixture, and the increase in the absorbance at 340 nm was measured. In addition, the calibration curve shown in FIG. 5 was made by repeating the above procedure using standard serum samples. Triglyceride contents in the above serum samples were determined from the calibration curve.

Figure 6:
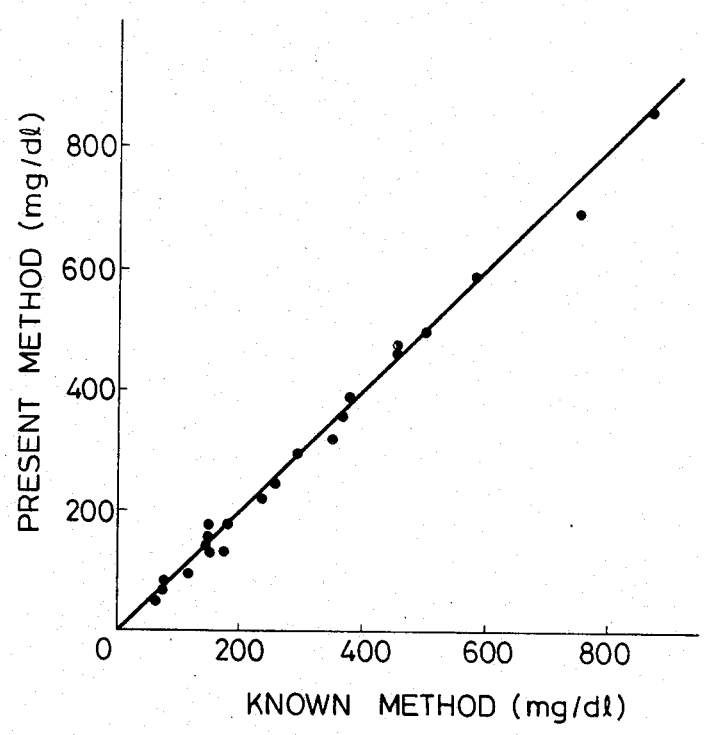
FIG. 6 shows the correlation between the triglyceride contents in serum samples determined according to the method of the invention and those determined according to a known method.

Further, comparison studies were carried out with serum samples between the method of the invention and the other known method [TG Kit-K (tradename), containing lipoprotein lipase, glycerol kinase, and glycerol-3-phosphate oxidase, supplied by Nihon Shoji Co., Ltd.]. As shown in FIG. 6, the correlation between the two-methods was excellent.

What is claimed is:

1. A method for enzymatic determination of glycerol, which comprises:
   incubating
   (a) a glycerol-containing sample;
   (b) a glycerol dehydrogenase;
   (c) a pyridine nucleotide coenzyme;
   (d) a dihydroxyacetone kinase in an amount sufficient to convert into dihdroxacetone phosphate and D-glyceraldehyde phosphate the dihydroxyacetone and D-glyceraldehyde produced by the action of glycerol dehydrogenase on the glycerol in said sample;
   (e) a phosphate donor; and
   (f) a divalent metal cation;
   determining the amount of resulting reduced pyridine nucleotide coenzyme; and
   determining the amount of glycerol from the amount of resulting reducted pyridine nucleotide coenzyme.

2. The method according to claim 1, wherein the glycerol in the sample is derived from triglyceride by the action of lipase.

3. The method according to claim 1, wherein the dihydroxyacetone kinase is derived from an organism of the genus *Schizosaccharomyces*.

4. The method according to claim 3, wherein said dihydroxyacetone kinase is derived from a strain of the microorganism selected from the group consisting of:
   *Schizosaccharomyces pombe* IFO 0340,
   *Schizosaccharomyces pombe* IFO 0354,
   *Schizosaccharomyces malidevoraus* IFO 1608,
   *Schizosaccharomyces japonicus* IFO 1609, and
   *Schizosaccharomyces octosporus* IAM 12257.

5. The method according to claim 1, wherein the amount of resulting reduced pyridine nucleotide coenzyme is determined by mearuring the absorption in the ultraviolet region.

6. A composition for enzymatic determination of glycerol, which comprises:
   a dihydroxyacetone kinase in an amount sufficient to convert into dihydroxyacetone phosphate and D-glyceraldehyde phosphate the dihdroxyacetone and D-glyceraldehyde produced by the action of glycerol dehydrogenase on the glycerol in said sample;
   a glycerol dehydrogenase;
   a pyridine nucleotide coenzyme;
   a phosphate donor; and
   a divalent metal cation.

7. The composition for enzymatic determination of glycerol according to claim 6, wherein the phosphate donor is adenosine-5'-triphosphate.

8. The composition for enzymatic determination of glycerol according to claim 3, wherein the divalent metal cation is selected from the group consisting of magnesium, calcium, cobalt, and manganese.

9. The composition for enzymatic determination of glycerol according to claim 6, which includes a buffer.

10. The composition according to claim 6, wherein said pyridine nucleotide coenzyme is selected from the group consisting of nicotinamide adenine dinucleotide and nicotinamide adenine dinucleotide phosphate.

11. The composition according to claim 6, wherein the dihydroxyacetone kinase is derived from an organism of the genus *Schizosaccharomyces*.

12. The composition according to claim 11, wherein said dihydroxyacetone kinase is derived from a strain of the microorganism selected from the group consisting of:
   *Schizosaccharomyes pombe* IFO 0340,
   *Schizosaccharomyes pombe* IFO 0354,
   *Schizosaccharomyes malidevoraus* IFO 1608,
   *Schizosaccharomyes japonicus* IFO 1609, and
   *Schizosaccharomyces octosporus* IAM 12257.

* * * * *